United States Patent
Takimiya et al.

(10) Patent No.: US 9,018,398 B2
(45) Date of Patent: Apr. 28, 2015

(54) INTERMEDIATE FOR ACENEDICHALCOGENOPHENE DERIVATIVE AND METHOD FOR SYNTHESIZING SAME

(71) Applicant: National University of Corporation Hiroshima University, Hiroshima (JP)

(72) Inventors: Kazuo Takimiya, Hiroshima (JP); Itaru Osaka, Hiroshima (JP)

(73) Assignee: National University of Corporation Hiroshima University, Hiroshima (JP)

( * ) Notice: Subject to any disclaimer, the term of this patent is extended or adjusted under 35 U.S.C. 154(b) by 0 days.

(21) Appl. No.: 14/379,250

(22) PCT Filed: Dec. 12, 2012

(86) PCT No.: PCT/JP2012/082241
§ 371 (c)(1),
(2) Date: Aug. 15, 2014

(87) PCT Pub. No.: WO2013/121664
PCT Pub. Date: Aug. 22, 2013

(65) Prior Publication Data
US 2015/0011780 A1    Jan. 8, 2015

(30) Foreign Application Priority Data
Feb. 16, 2012   (JP) .................. 2012-031605

(51) Int. Cl.
| | | |
|---|---|---|
| *C07D 333/74* | (2006.01) | |
| *C07F 7/08* | (2006.01) | |
| *C07F 11/00* | (2006.01) | |
| *C07F 7/22* | (2006.01) | |

(52) U.S. Cl.
CPC .............. *C07F 7/0812* (2013.01); *C07F 11/00* (2013.01); *C07F 7/0814* (2013.01); *C07F 7/2212* (2013.01)

(58) Field of Classification Search
CPC ................................ C07D 333/74; C07F 7/08
USPC ............................................. 549/42, 43, 213
See application file for complete search history.

(56) References Cited

U.S. PATENT DOCUMENTS 7,834,198 B2 * 11/2010 Takimiya et al. ................ 549/42
8,816,100 B2 *  8/2014 Takimiya ........................ 549/42

FOREIGN PATENT DOCUMENTS

| JP | 2009508807 | 3/2009 |
|---|---|---|
| JP | 2009267134 | 11/2009 |
| JP | 2009267140 | 11/2009 |
| JP | 2010018529 | 1/2010 |
| TW | 200821317 | 5/2008 |
| TW | 201139505 | 11/2011 |
| TW | 201141902 | 12/2011 |
| WO | WO-2011115938 | 9/2011 |

OTHER PUBLICATIONS

Nakano, Masahiro et al., "Borylation on Benzo and Naphtho dichalcogenophenes: Different Chalcogene Atom Effects on Borylation Reaction Depending on Fused Ring Structure", Japan (2012).
Shimizu, Masaki et al., "Palladium-catalyzed double cross-coupling reaction of 1,2-bis(pinacolatoboryl) alkenes and -arenes with 2,2'-dibromobiaryls: annulative approach to functionalized polycyclic aromatic hydrocarbons", Japan (2011).
Shinamura, et al., "Synthesis and Structure Property Relationship of Naphthodithiophene Derivities", 90th Annual Meeting of the Chemical Society of Japan in Spring, 2010.
Shinamura, Shoji et al., "Orthogonally Functionalized Naphodithiophenes: Selective Protection and Borylation", Japan (2012).

* cited by examiner

*Primary Examiner* — Golam M M Shameem
(74) *Attorney, Agent, or Firm* — Michael A. Glenn; Perkins Coie LLP

(57) ABSTRACT

An intermediate for an acenedichalcogenophene derivative is expressed by formula (1) or formula (2).

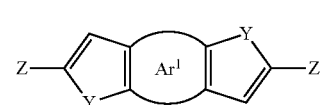

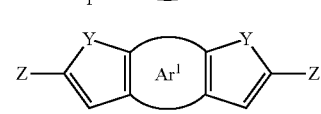

In the formulae (1) and (2), $Ar^1$ represents any one ring of a benzene ring, a naphthalene ring, or an anthracene ring having at least one of hydrogen thereof is substituted with a boronic acid group or a boronate ester group; Y represents an oxygen atom, a sulfur atom, or a selenium atom; and Z represents a substituent group. This intermediate for the acenedichalcogenophene derivative is capable of easily deprotecting the boronic acid group or the boronate ester group and allowing a substitution with a desired functional group, such that a desired synthesis of acenedichalcogenophene derivative, and further a desired synthesis of oligomers and polymers using this obtained acenedichalcogenophene derivative can be achieved.

4 Claims, No Drawings

INTERMEDIATE FOR ACENEDICHALCOGENOPHENE DERIVATIVE AND METHOD FOR SYNTHESIZING SAME

TECHNICAL FIELD

The present disclosure relates to an intermediate for an acenedichalcogenophene derivative and a method for synthesizing the same.

BACKGROUND ART

Recently, attention has been drawn to compounds having acenedichalcogenophene as a basic skeleton such as naphthodithiophene, benzodithiophene, anthradithiophene, and the like especially as materials for organic semiconductors due to their high electron mobility, the high on/off current ratio, and the excellent storage stability (for example, Patent Literatures 1 and 2).

CITATION LIST

Patent Literature

Patent Literature 1: Unexamined Japanese Patent Application Kokai Publication No. 2009-267134
Patent Literature 2: Unexamined Japanese Patent Application Kokai Publication No. 2009-267140

SUMMARY OF INVENTION

Technical Problem

Essentially, obtaining the organic semiconductor materials having acenedichalcogenophene as a basic skeleton relies on efficiency and selectivity of obtaining the acenedichalcogenophene derivatives. However, sufficient research has not been conducted for the compounds having the acenedichalcogenophene as the basic skeleton due to their difficulty in carrying out synthesis, and other such reasons.

It is therefore an object of the present disclosure to provide intermediates for acenedichalcogenophene derivatives that are advantageous in synthesizing organic semiconductor materials, and a method for synthesizing the same.

Solution to Problem

According to a first aspect of the present disclosure, there is provided an intermediate for an acenedichalcogenophene derivative of formula (1) or formula (2),

[Chemical formula 1]

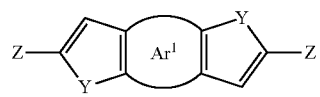
(1)

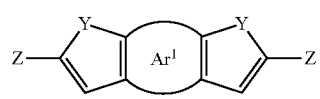
(2)

(in the formulae (1) and (2), $Ar^1$ represents any one ring of a benzene ring, a naphthalene ring, and an anthracene ring having at least one of hydrogens thereof is substituted with a boronic acid group or a boronate ester group; Y represents an oxygen atom, a sulfur atom, or a selenium atom; and Z represents a substituent group).

Preferably, the acenedichalcogenophene derivative expressed by the formula (1) is expressed by formula (11), formula (21), formula (22) or formula (23).

[Chemical formula 2]

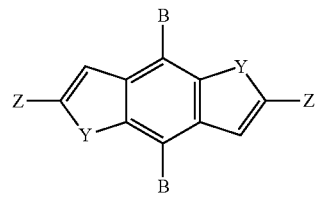
(11)

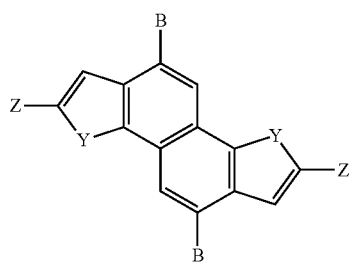
(21)

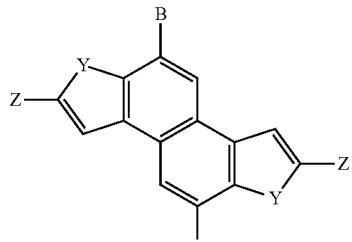
(22)

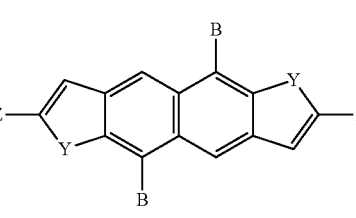
(23)

(In the formulae (11), (21), (22) and (23), B represents a boronate ester group, and Y and Z are as defined for the formula (1).)

A preferred formula for the substituent group is any one of formulae from (41) to (45).

[Chemical formula 3]

(41)

(42)

(43)

(44)

(45)

(In the formulae (41) to (45), R represents an alkyl group, an aryl group, or a phenylmethyl group, and X represents harogen.)

Further, the boronate ester group is preferably a pinacol boronate ester group.

According to a second aspect of the present disclosure, a method for synthesizing an intermediate for an acenedichalcogenophene derivative includes a reaction of a compound expressed by either formula (51) or formula (52) with a boronic acid or a boronate ester,

[Chemical formula 4]

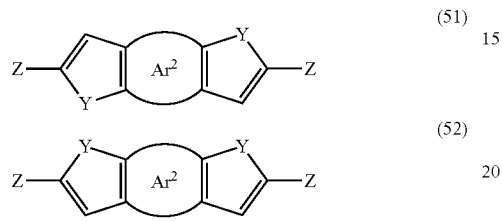

(in formulae (51) and (52), $Ar^2$ represents any one ring of a benzene ring, a naphthalene ring, or an anthracene ring; Y represents an oxygen atom, a sulfur atom, or a selenium atom; and Z represents a substituent group), and at least one of hydrogens in the benzene ring, the naphthalene ring, or the anthracene ring is substituted with a boronic acid group or a boronate ester group, such that an intermediate for acenedichalcogenophene derivative expressed by formula (1) or formula (2) is synthesized,

[Chemical formula 5]

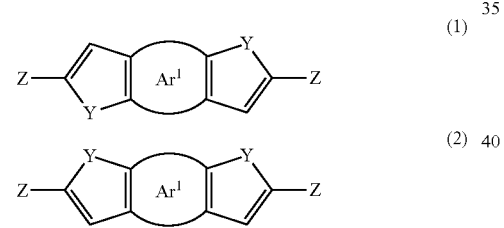

(in formulae (1) and (2), $Ar^1$ represents any one ring of a benzene ring, a naphthalene ring, or an anthracene ring having at least one of hydrogen thereof is substituted with a boronic acid group or a boronate ester group, and Y and Z are as defined in the formulae (51) and (52)).

An addition of a CH activation catalyst is preferred as a catalyst.

As for the boronate ester, pinacol boronate ester is preferably employed.

It is also preferred to carry out the synthesis of the compounds expressed by the formula (51) or the formula (52) by reacting compounds expressed by formula (61) or formula (62) with electrophiles, and introducing a substituent group into the α-position.

[Chemical formula 6]

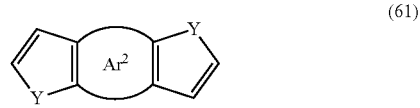

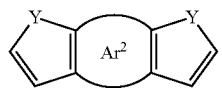

(In the formulae (61) and (62), $Ar^2$ and Y are as defined for the formulae (51) and (52).)

An addition of organometallic reagents is also preferred.

As for the electrophiles, any one of formulae (71) to (75) is preferably used.

[Chemical formula 7]

(In the formulae (71) to (75), R represents an alkyl group, an aryl group, or a phenylmethyl group, and X represents halogen.)

Advantageous Effects of Invention

The intermediate for the acenedichalcogenophene derivative according to the present disclosure has its acene coupled with a boronic acid group or a boronate ester group. The intermediate for the acenedichalcogenophene derivative is capable of easily deprotecting the boronic acid group or the boronate ester group thereby desired functional group substitution is achieved. With this intermediate for the acenedichalcogenophene derivative, a desirable synthesis of an acenedichalcogenophene derivative can be carried out, and further, and by using such acenedichalcogenophene derivative obtained, a desirable oligomer or a polymer synthesis can be achieved. By this, research, developments and practical applications of materials, for example, for organic semiconductors having a novel acenedichalcogenophene skeleton are facilitated.

Further, the method for synthesizing the intermediate for the acenedichalcogenophene derivative according to the present disclosure introduces a substituent group into the α-position at which a preferential substitution occurs in boronization of the acenedichalcogenophene. This allows the boronization to be performed selectively at any desirable position of the acene, thereby the desirable intermediate for the acenedichalcogenophene derivative can be obtained.

DESCRIPTION OF EMBODIMENTS

According to an embodiment, an intermediate for an acenedichalcogenophene derivative is expressed by formula (1) or formula (2).

[Chemical formula 8]

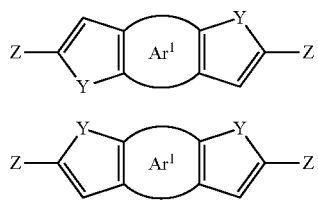

(1)

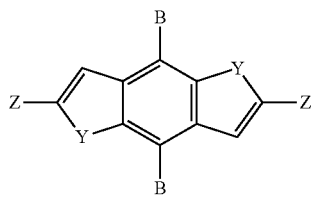

(2)

In formulae (1) and (2), $Ar^1$ represents any one ring of a benzene ring, a naphthalene ring, and an anthracene ring having at least one of hydrogens substituted with a boronic acid group or a boronate ester group. In the formulae (1) and (2), Y represents an oxygen atom, a sulfur atom, or a selenium atom. Further in the formulae (1) and (2), Z represents a substituent group.

The formulae (1) and (2) are not limited to chalcogenophene-$Ar^1$-chalcogenophene having a structure of fused straight line, and that a structure of a fused polygonal line may be employed as well.

Examples of an intermediate for a benzochalcogenophene derivative are given in following formulae (11) to (15).

[Chemical formula 9]

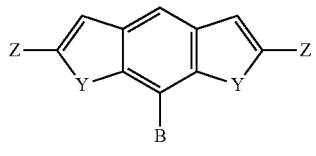

(11)

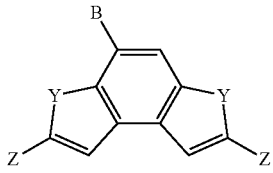

(12)

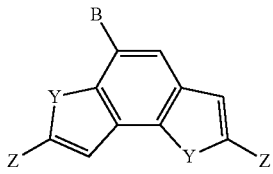

(13)

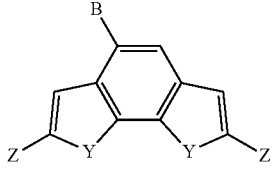

(14)

(15)

Examples of an intermediate for a naphthodichalcogenophene derivative are given in following formulae (21) to (24).

[Chemical formula 10]

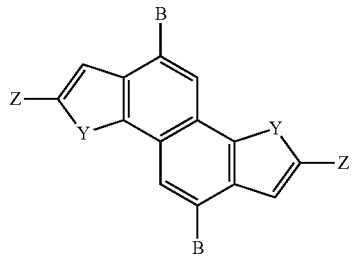

(21)

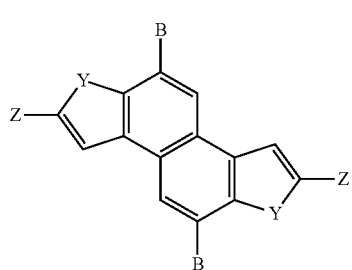

(22)

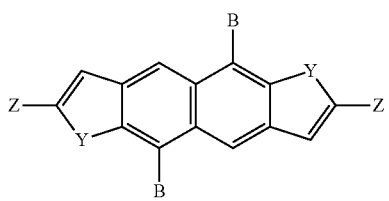

(23)

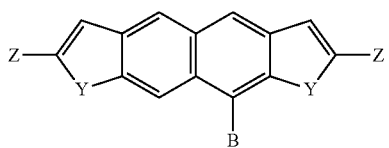

(24)

Examples of an intermediate for an anthradichalcogenophene derivative are given in following formulae (31) to (37).

[Chemical formula 11]

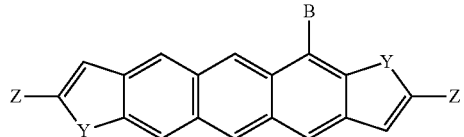

(31)

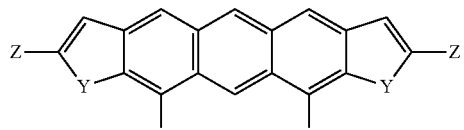

(32)

(33)
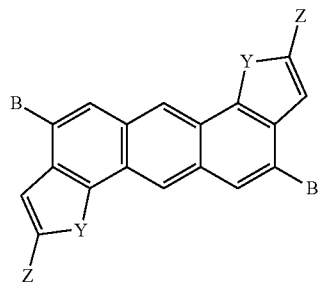

(34)
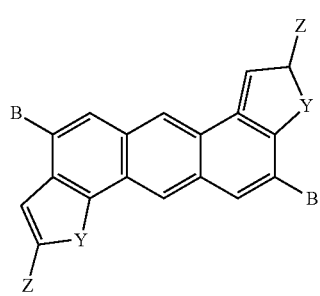

(35)
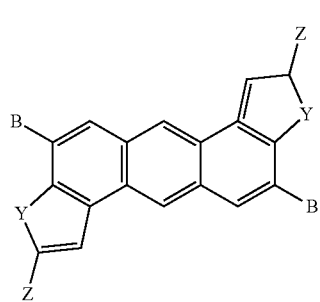

(36)
(37)
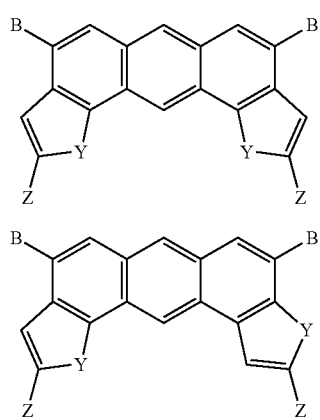

In the formulae (11) to (15), the formulae (21) to (24), and the formulae (31) to (37), B denotes a boronic acid group or a boronate ester group. The boronic acid group or the boronate ester group is not limited to any particular group, and that a pinacol boronate ester group, for example, may be employed.

The substituent group is not limited to any particular group, and functional groups, for example, given by formulae (41) to (45) may be employed. In the formulae (41) to (45), R represents an alkyl group, an aryl group, or a phenylmethyl group, and X represents halogen.

[Chemical formula 12]

—R  (41)

—SiR$_3$  (42)

$$\overset{O}{\underset{\|}{-C}}-R$$  (43)

$$\overset{O}{\underset{\|}{-C}}-OR$$  (44)

—X  (45)

The aforementioned intermediate for the acenedichalcogenophene derivative is capable of being easily deprotected using various operations, such that the substituent group can be substituted with halogen, a hydroxyl group, hydrogen, or the like. Therefore, synthesis of an oligomer or a polymer having an acenedichalcogenophene skeleton as a basic skeletal structure can be carried out.

Compounds having the acenedichalcogenophene as the basic skeletal structure have a potential for exhibiting excellent electron mobility. Based on such intermediates for the acenedichalcogenophene derivative, research, developments, and practical applications of oligomers and polymers that are useful in various organic semiconductor materials can be facilitated.

For example, by using an example of the intermediate for the acenedichalcogenophene derivative above, 2,7-ditriisoprophylsilyl-5,10-bis[(pinacolate)boryl]-naphtho[1,2-b:5,6-b']dithiophene, a synthesis of a polymeric compound 1 is carried out via the following scheme.

[Chemical formula 13]

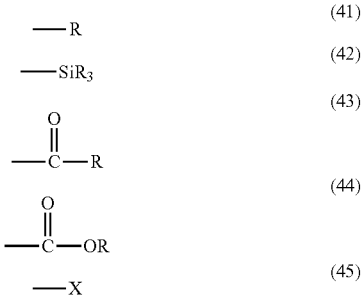

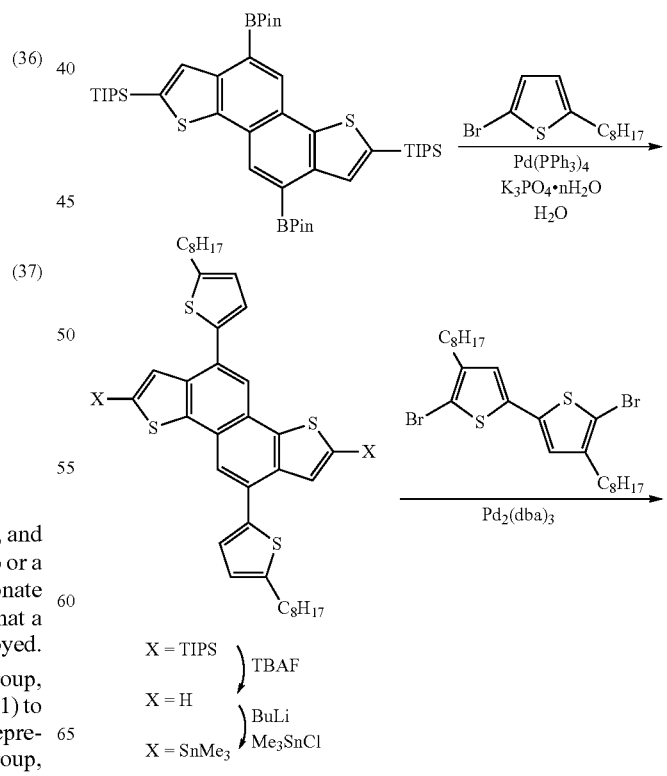

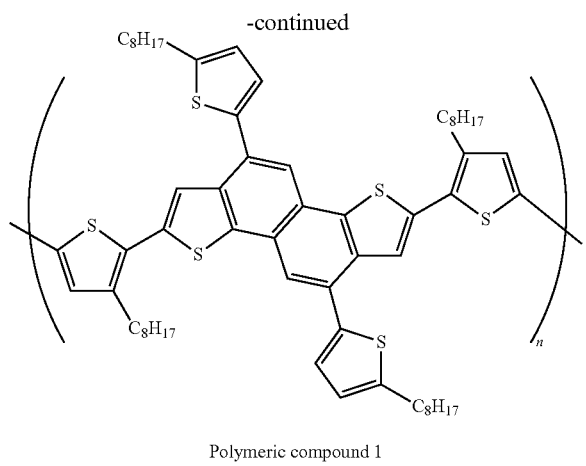

Polymeric compound 1

Hereinafter, a method for synthesizing the aforementioned intermediate for the acenedichalcogenophene derivative is described.

The acenedichalcogenophene having a substituent group in the α-position expressed by the formula (51) or the formula (52) is reacted with a boronic acid or a boronate ester. In the formulae (51) and (52), $Ar^2$ is any one ring of a benzene ring, a naphthalene ring, or an anthracene ring, and having a structure of chalcogenophene-$Ar^2$-chalcogenophene in a fused straight line or a polygonal line. In addition, Y denotes an oxygen atom, a sulfur atom, or a selenium atom, and Z denotes a substituent group.

[Chemical formula 14]

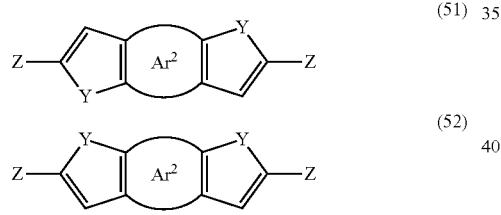

As a result, some of the hydrogens in the benzene ring, the naphthalene ring, the anthracene ring are substituted by a boronic acid group or a boronate ester group, so that the intermediate for the acenedichalcogenophene derivative expressed by the aforementioned formula (1) or the formula (2) can be obtained.

[Chemical formula 15]

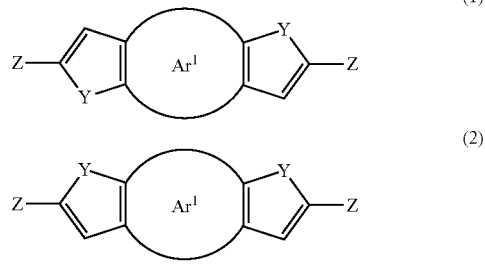

A more specific example of the method for synthesizing the intermediate for the acenedichalcogenophene derivative is described. The acenedichalcogenophene having a substituent group in the α-position expressed by the formula (51) or the formula (52), a boronic acid or a boronate ester, and the CH activation catalyst are placed in a solution such as a dried cyclohexane solution of 4,4'-di-t-butyl-2,2'-bipyridine, which is then stirred for a predetermined period of time (for example, about 10 hours) under argon atmosphere, shielded light, and at predetermined temperature (for example, about 80° C.). After the reaction mixture is cooled, the catalyst is removed by distillation, and a residue is dissolved in chloroform, or the like, and purified by column chromatography, so that the intermediate for the acenedichalcogenophene derivative is obtained.

Due to naphthodichalcogenophene that is substituent-introduced in the α-position, where the preferential boronization takes place, being boronized, some of hydrogens in the benzene ring, the naphthalene ring, and the anthracene ring can be selectively boronized.

There is no particular limitation on the boronic acid and the boronate ester that are used, and thus, for example, a pinacol boronate ester such as pinacol diborane may be used.

Further, addition of a CH activation catalyst is preferred. As for the CH activation catalyst, a transition metal such as palladium, iridium, or ruthenium, or a catalyst that contains such transition metal may be used.

Compounds having a substituent group in the α-position expressed by formula (51) or formula (52) can be synthesized, for example, by the following way.

Unsubstituted acenedichalcogenophene expressed by formula (61) or formula (62) is reacted with electrophiles. In formula (61) and formula (62), $Ar^2$ and Y are as defined in formula (51) and formula (52).

[Chemical formula 16]

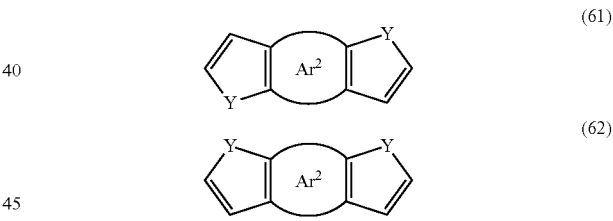

Due to this, a substituent group can be introduced into the α-position of each compound expressed by formula (61) or formula (62), and thus, the compounds expressed by the aforementioned formula (51) or formula (52) can be obtained.

Now, more specific examples of the method for synthesizing the compounds expressed by formula (51) or formula (52) are described. Unsubstituted acenedichalcogenophene is placed in a THF (tetrahydrofuran) solution or the like, which is added to a solution containing an organometallic reagent mixed with hexane, which is then stirred. After the electrophiles are added to this reaction mixture and then stirred, this is further diluted with water, and hydrochloric acid or the like is added thereto. Further, a precipitate that is formed is separated using filtration or the like, then the precipitate is washed with methanol, hexane, or the like, thereby target compounds expressed by formula (51) or formula (52) are obtained.

There is no particular limitation on the electrophiles used as long as which is able to functionally substituted at the α-position of chalcogenophene, therefore, for example, halogen compounds expressed by formulae (71) to (75) can be used. In formulae (71) to (75), R denotes an alkyl group, an aryl group or a phenylmethyl group, and X denotes halogen.

[Chemical formula 17]

$$X-R \quad (71)$$

$$X-SiR_3 \quad (72)$$

$$X-\overset{O}{\underset{\|}{C}}-R \quad (73)$$

$$X-\overset{O}{\underset{\|}{C}}-OR \quad (74)$$

$$X-X \quad (75)$$

Preferably, an organometallic reagent such as BuLi may be used to accelerate the reaction above. The organometallic reagents are not limited to any particular reagents as long as capable of accelerating the reactions.

Description of Embodiments

Hereinafter, examples of a synthesis of an intermediate for acenedichalcogenophene derivative from unsubstituted acenedichalcogenophene, and further, deprotection of the obtained intermediate for the acenedichalcogenophene derivative, and functionalization thereof are described.

Firstly, triisopropylsilyl-substituted naphthodichalcogenophene was synthesized using various unsubstituted naphthodichalcogenophene.

Example of Synthesis 1

Synthesis of 2,7-bis(triisopropylsilyl)naphtho[1,2-b:5,6-b']dithiophene (Hereinafter, the Compound A1)

An n-BuLi (3 mmol) hexane solution was added to a THF (10 ml) solution of naphtho[1,2-b:5,6-b']dithiophene (1 mmol), and stirred at room temperature for one hour. This reaction mixture was slowly added with triisopropylsilyl chloride (4 mmol), and further, stirred at room temperature for 16 hours. Further, diluted with water (50 ml), and 1N hydrochloric acid (50 ml) was added. A precipitate formed was filtered out and washed with water, methanol, or hexane such that the compound A1 was obtained as a white solid.

[Chemical formula 18]

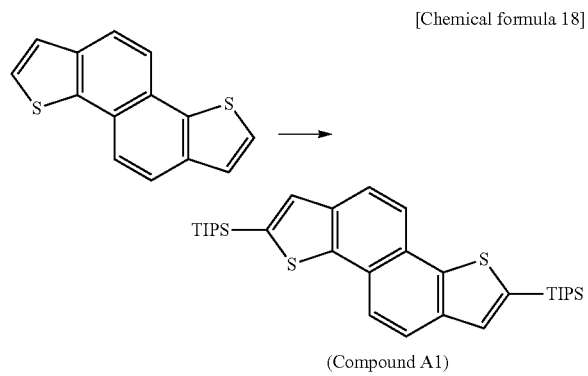

(Compound A1)

Measurement data of the compound A1 obtained is given below.

Quantitative yield. $^1$H-NMR (500 MHz, CDCl$_3$) δ 1.19 (d, 36H, CH$_3$), 1.47 (sept, 6H, CH), 7.64 (s, 2H, ArH), 7.93 (d, 2H, ArH), 8.07 (d, 2H, ArH); EIMS (70 eV) m/z 552 (M$^+$); Anal. Calcd for C$_{32}$H$_{48}$S$_2$Si$_2$: C, 69.50; H, 8.75. Found: C, 69.35; H, 9.05%.

Example of Synthesis 2

Synthesis of 2,7-bis(triisopropylsilyl)naphtho[1,2-b:5,6-b']difuran (Hereinafter, the Compound B1)

Other than using naphtho[1,2-b:5,6-b']difuran instead of naphtho[1,2-b:5,6-b']dithiophene the compound B1 was obtained in the same way described in Example of Synthesis 1.

[Chemical formula 19]

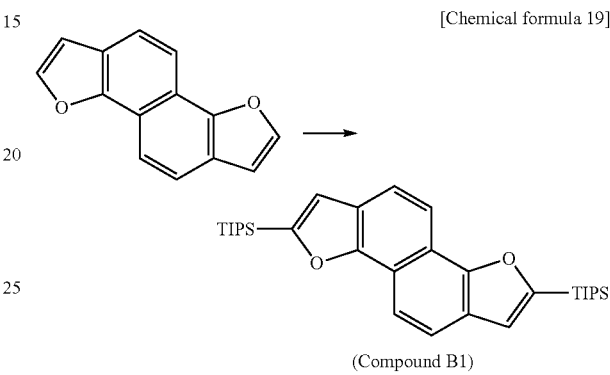

(Compound B1)

Measurement data for the compound B1 obtained is given below.

Quantitative yield. $^1$H-NMR (500 MHz, CDCl$_3$) δ 1.20 (d, 36H, CH$_3$), 1.46 (sept, 6H, CH), 7.19 (s, 2H, ArH), 7.75 (d, 2H, ArH), 8.15 (d, 2H, ArH), $^{13}$C NMR δ 11.3, 18.8, 115.7, 119.0, 119.3, 119.9, 123.1, 154.6, 159.7; EIMS (70 eV) m/z 520 (M$^+$).

Example of Synthesis 3

Synthesis of 2,7-bis(triisopropylsilyl)naphtho[1,2-b:5,6-b']diselenophene (Hereinafter, the Compound C1)

Other than using naphtho[1,2-b:5,6-b']diselenophene instead of naphtho[1,2-b:5,6-b']dithiophene, the compound C1 was obtained in the same way described in Example of Synthesis 1.

[Chemical formula 20]

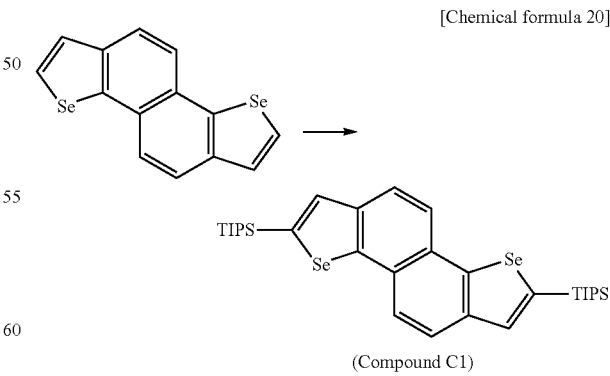

(Compound C1)

Measurement data for the compound C1 obtained is given below.

89% yield. $^1$H-NMR (500 MHz, CDCl$_3$) δ 1.19 (d, 36H, CH$_3$), 1.43 (sept, 6H, CH), 7.89 (d, 2H, ArH), 7.92 (s, 2H, ArH), 7.92 (d, 2H, ArH); EIMS (70 eV) m/z 648 (M$^+$).

Example of Synthesis 4

Synthesis of 2,7-bis(triisopropylsilyl)naphtho[2,1-b:6,5-b']dithiophene (Hereinafter, the Compound D1)

As is indicated in the chemical formula below, other than using naphtho[2,1-b:6,5-b']dithiophene instead of naphtho[1,2-b:5,6-b']dithiophene, the compound D1 was obtained in the same way described in Example of Synthesis 1.

[Chemical formula 21]

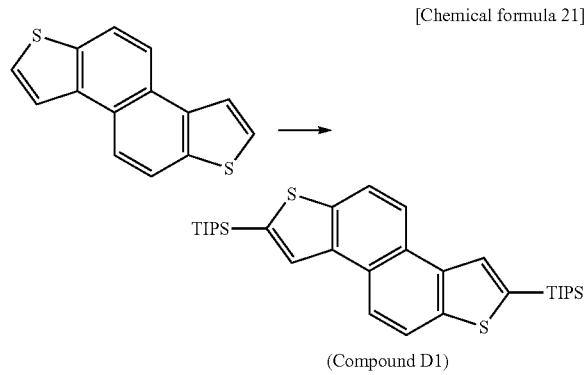

(Compound D1)

Measurement data for the compound D1 obtained is given below.

67% yield; $^1$H NMR (400 MHz CDCl$_3$) δ 1.19 (d, J=7.4 Hz, 36H), 1.49 (sept, J=7.4 Hz, 6H), 8.03 (d, J=8.8 Hz, 2H), 8.17 (s, 2H), 8.32 (d, J=8.8 Hz, 2H); $^{13}$C NMR (400 MHz CDCl$_3$) δ 12.1, 18.8, 120.7, 120.7, 126.4, 130.5, 136.6, 138.0, 141.1; MS m/z=552 (M$^+$) Anal. Calcd for C$_{32}$H$_{48}$S$_2$Si$_2$: C, 69.50; H, 8.75%. Found: C, 69.74; H, 8.56%.

Example of Synthesis 5

Synthesis of 2,7-bis(triisopropylsilyl)naphtho[2,3-b:6,7-b']dithiophene (Hereinafter, the Compound E1)

Other than using naphtho[2,3-b:6,7-b']dithiophene instead of naphtho[1,2-b:5,6-b']dithiophene, the compound E1 was obtained in the same way described in Example of Synthesis 1.

[Chemical formula 22]

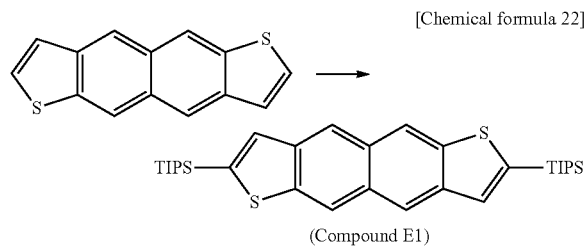

(Compound E1)

Measurement data for the compound E1 obtained is given below.

97% yield; $^1$H NMR (500 MHz, CDCl$_3$) δ 1.19 (d, J=7.5 Hz, 36H, CH3), 1.45 (sept, J=7.5 Hz, 6H, CH), 7.58 (s, 2H, ArH), 8.39 (s, 2H, ArH), 8.48 (s, 2H, ArH); EIMS (70 eV) m/z 552 (M$^+$).

Each triisopropylsilyl-substituted naphtho[1,2-b:5,6-b'] dichalcogenophene obtained in the aforementioned Examples of Synthesis 1 to 5 (the compounds A1, B1, C1, D1, and E1) was directly boronized, and then each corresponding intermediate for the dichalcogenophene derivative was synthesized.

Example of Synthesis 6

Synthesis of 5,10-bis(4,4,5,5-tetramethyl-1,3,2-dioxaborolan-2-yl)-2,7-bis(triisopropylsilyl)naphtho[1,2-b:5,6-b']dithiophene (Hereinafter, the Compound A2)

A dried cyclohexane solution of the compound A1 (1 mmol), pinacol diborane (2 mmmol), [Ir(OMe)(COD)]$_2$ (5 mol %), and 4,4'-di-t-butyl-2,2'-bipyridine (10 mol %) was stirred for 10 hours under argon atmosphere and shielded light at 80° C. After the reaction mixture was cooled, a solvent was removed by distillation. A residue was dissolved in chloroform, purified using column chromatography (silica gel, chloroform), and obtained the compound A2 as a white solid.

[Chemical formula 23]

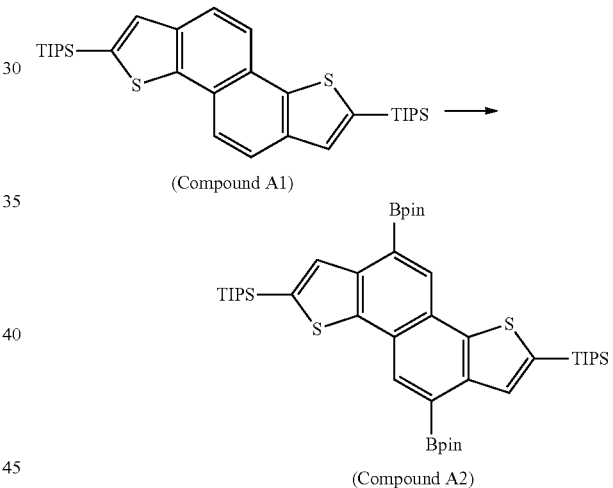

Measured data for the compound A2 obtained is given below

Quantitative yield. $^1$H-NMR (500 MHz, CDCl$_3$) δ 1.22 (d, 36H, CH$_3$), 1.45 (s, 24H, CH$_3$), 1.47 (sept, 6H, CH), 8.40 (s, 2H, ArH), 8.58 (s, 2H, ArH) $^{13}$C NMR δ 12.2, 18.9, 25.2, 84.1, 126.7, 130.5, 134.5, 136.2, 142.1, 143.0; EIMS (70 eV) m/z 804 (M$^+$); Anal. Calcd for C$_{44}$H$_{70}$B$_2$O$_4$S$_2$Si$_2$: C, 65.65; H, 8.77. Found: C, 65.28; H, 9.16%.

Example of Synthesis 7

Synthesis of 5,10-bis(4,4,5,5-tetramethyl-1,3,2-dioxaborolan-2-yl)-2,7-bis(triisopropylsilyl)naphtho[1,2-b:5,6-b']difran (Hereinafter, the Compound B2)

Other than using the compound B1 instead of the compound A1, the compound B2 was obtained in the same way described in Example of Synthesis 6.

[Chemical formula 24]

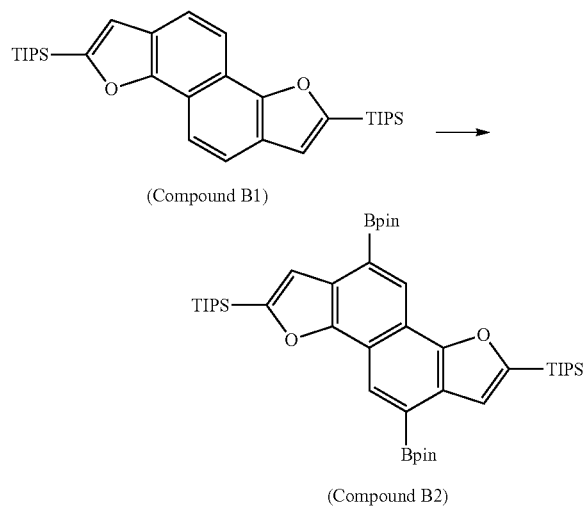

(Compound B1)

(Compound B2)

Measurement data for the compound B2 obtained is given below.

86% yield. $^1$H-NMR (500 MHz, CDCl$_3$) δ 1.22 (d, 36H, CH$_3$), 1.45 (s, 24H, CH$_3$), 1.51 (sept, 6H, CH), 7.60 (s, 2H, ArH), 8.61 (s, 2H, ArH) $^{13}$C NMR δ 11.4, 18.9, 25.2, 84.0, 120.1, 121.1, 124.0, 127.0, 154.2, 159.4; EIMS (70 eV) m/z 772 (M$^+$).

Example of Synthesis 8

Synthesis of 5,10-bis(4,4,5,5-tetramethyl-1,3,2-dioxaborolan-2-yl)-2,7-bis(triisopropylsilyl)naphtho[1,2-b:5,6-b']diselenophene (Hereinafter, the Compound C2)

Other than using the compound C1 instead of the compound A1, the compound C2 was obtained in the same way described in Example of Synthesis 6.

[Chemical formula 25]

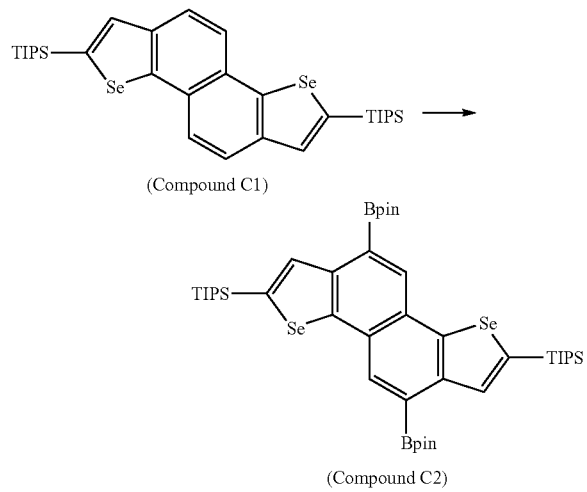

(Compound C1)

(Compound C2)

Measurement data for the compound C2 obtained is given below.

Quantitative yield. $^1$H-NMR (500 MHz, CDCl$_3$) δ 1.22 (d, 36H, CH$_3$), 1.43 (s, 24H, CH$_3$), 1.43 (sept, 6H, CH), 8.45 (s, 2H, ArH), 8.78 (s, 2H, ArH) $^{13}$C NMR δ 12.4, 18.9, 25.2, 84.1, 129.0, 133.2, 139.6, 140.0, 144.8, 146.8; EIMS (70 eV) m/z 900 (M$^+$).

Example of Synthesis 9

Synthesis of 5,10-bis(4,4,5,5-tetramethyl-1,3,2-dioxaborolan-2-yl)-2,7-bis(triisopropylsilyl)naphtho[2,1-b:6,5-b']dithiophene (Hereinafter, the Compound D2)

Other than using the compound D1 instead of the compound A1, the compound D2 was obtained in the same way described in Example of Synthesis 6.

[Chemical formula 26]

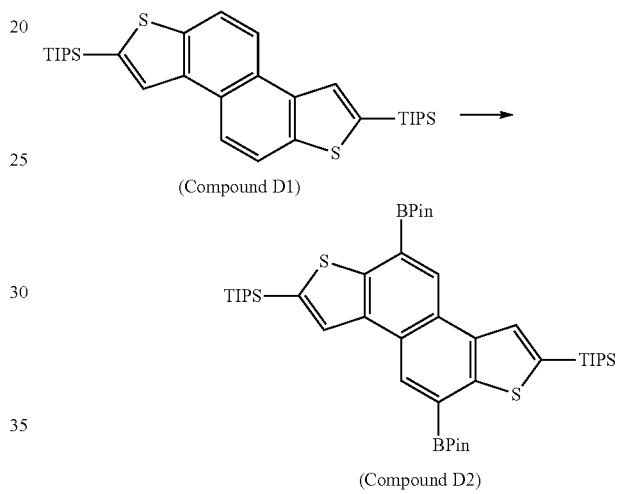

(Compound D1)

(Compound D2)

Measurement data for the compound D2 obtained is given below.

99% yield; $^1$H NMR (400 MHz CDCl$_3$) δ 1.22 (d, J=7.4 Hz, 36H), 1.49 (s, 24H), 1.56 (sept, J=7.4 Hz, 6H), 8.27 (s, 2H), 8.78 (s, 2H); $^{13}$C NMR (400 MHz CDCl$_3$) δ 12.1, 19.0, 25.2, 84.6, 127.5, 129.1, 130.3, 130.3, 137.3, 137.8, 145.9; MS m/z=804 (M$^+$).

Example of Synthesis 10

Synthesis of 5,10-bis(4,4,5,5-tetramethyl-1,3,2-dioxaborolan-2-yl)-2,7-bis(triisopropylsilyl)naphtho[2,3-b:6,7-b']dithiophene (Hereinafter, the Compound E2)

Other than using the compound E1 instead of the compound A1, the compound E2 was obtained in the same way described in Example of Synthesis 6.

[Chemical formula 27]

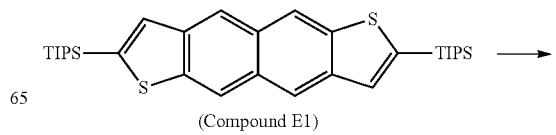

(Compound E1)

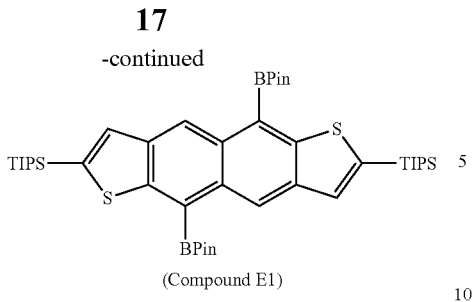

(Compound E1)

Measurement data for the compound E2 obtained is given below.

42% yield; $^1$H NMR (500 MHz, CDCl$_3$) δ 1.20 (d, J=7.5 Hz, 36H, CH$_3$), 1.46 (sept, J=7.5 Hz, 6H, CH), 1.56 (s, 24H, CH$_3$), 7.59 (s, 2H, ArH), 9.33 (s, 2H, ArH); EIMS (70 eV) m/z=804 (M$^+$).

Further, the substituent group of the compound A2 obtained in Example of Synthesis 6 was deprotected, and various functionalizations were carried out.

Example of Synthesis 11

Synthesis of 5,10-dibromo-2,7-bis(triisopropylsilyl) naphtho[1,2-b:5,6-b']dithiophene (Hereinafter, the Compound A3a)

The compound A2 (1.6 g, 2.0 mmol) and CuBr$_2$ (2.7 g, 12 mmol) were suspended in 200 ml of an NMP/methanol/water mixture solution (volume ratio 5/2/1), and refluxed for 15 hours. After being cooled, the reaction mixture was poured into 1N hydrochloric acid (100 ml), and then a precipitate formed was filtered out. By washing this with hexane, a target compound A3a was obtained as a white solid (1.4 g, 96%).

[Chemical formula 28]

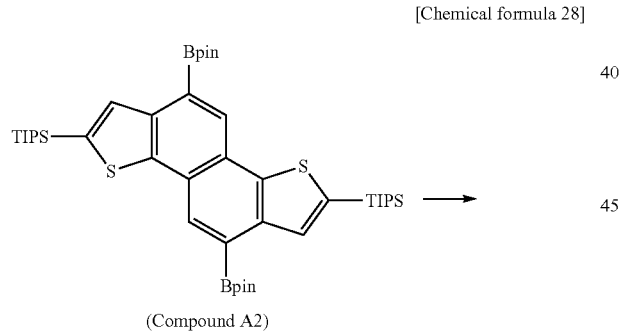

Measurement data for the compound A3a obtained is given below.

$^1$H NMR (500 MHz, CDCl$_3$) δ, 1.19 (d, 36H, CH$_3$), 1.48 (sept, 6H, CH), 7.74 (s, 2H, ArH), 8.21 (s, 2H, ArH) $^{13}$C NMR δ 12.0, 18.8, 116.6, 123.9, 125.5, 133.9, 137.1, 138.6, 142.2; EIMS (70 eV) m/z 708 (M$^+$); Anal. Calcd for C$_{32}$H$_{46}$Br$_2$S$_2$Si$_2$: C, 54.07; H, 6.52. Found: C, 54.29; H, 6.31%.

Example of Synthesis 12

Synthesis of 5,10-dichloro-2,7-bis(triisopropylsilyl) naphtho[1,2-b:5,6-b']dithiophene (Hereinafter, the Compound A3b)

Other than using CuCl$_2$ instead of CuBr$_2$ the compound A3b (isolated yield of 94%) was prepared in the same way described in Example of Synthesis 11.

[Chemical formula 29]

Measurement data for the compound A3b obtained is given below.

$^1$H NMR (500 MHz, CDCl$_3$) δ, 1.19 (d, 36H, CH$_3$), 1.48 (sept, 6H, CH), 7.77 (s, 2H, ArH), 8.02 (s, 2H, ArH) $^{13}$C NMR δ 12.0, 18.8, 120.3, 124.9, 127.7, 131.9, 137.3, 137.3, 142.9; EIMS (70 eV) m/z 620 (M$^+$).

Example of Synthesis 13

Synthesis of 5,10-dicyano-2,7-bis(triisopropylsilyl) naphtho[1,2-b:5,6-b']dithiophene (Hereinafter, the Compound A3c)

The compound A2 (402 mg, 0.5 mmol), CsF (152 mg, 10 mmol), Zn(CN)$_2$ (352 mg, 3.0 mmol) and Cu(II)No$_3$.3H$_2$O (483 mg, 2.0 mmol) were refluxed in an 80 ml dioxane-methanol-water (volume ratio 5/2/1) mixture solution for three days. After being cooled, the reaction mixture was extracted with chloroform, then a concentrated organic phase was purified using column chromatography (silica gel, chloroform), and the compound A3c was obtained as an yellow solid (67 mg, 22%).

[Chemical formula 30]

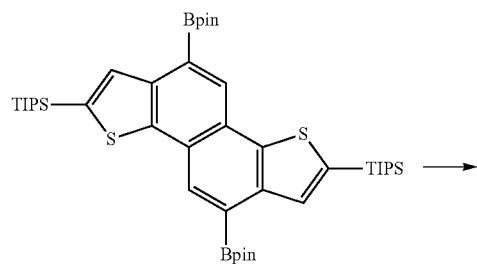

(Compound A2)

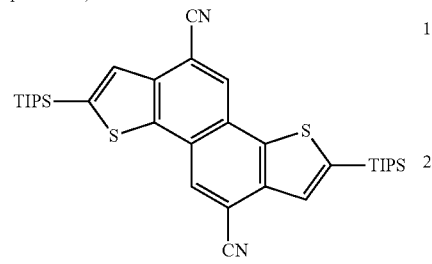

(Compound A3c)

Measurement data for the compound A3c obtained is given below.

$^1$H NMR (500 MHz, CDCl$_3$) δ, 1.19 (d, 36H, CH$_3$), 1.50 (sept, 6H, CH), 7.85 (s, 2H, ArH), 8.49 (s, 2H, ArH) $^{13}$C NMR δ 11.9, 18.7, 108.2, 117.6, 126.0, 127.5, 131.5, 137.6, 140.8, 143.7; EIMS (70 eV) m/z 602 (M$^+$).

Example of Synthesis 14

Synthesis of 5,10-dihydroxy-2,7-bis(triisopropylsilyl)naphtho[1,2-b:5,6-b']dithiophene (Hereinafter, the Compound A3d)

The compound A2 (1.6 g, 2.0 mmol) and oxone (6.9 g, 11 mmol) were added to a mixture of solution containing THF (120 ml), acetone (24 ml) and water (12 ml) under argon atmosphere. Under the shielded light, this mixture was stirred at room temperature for 15 hours, followed by addition of a saturated Na$_2$S$_2$O$_4$ aqueous solution and then the reaction was stopped. After the solvent was removed by distillation, a residue was extracted using ethyl acetate, and subsequently an organic phase was concentrated, and purified by column chromatography (silica gel, chloroform), and the compound A3d (1.1 g, 91%) was obtained.

[Chemical formula 31]

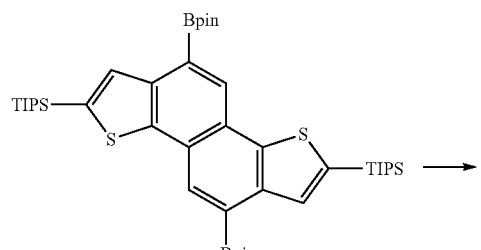

(Compound A2)

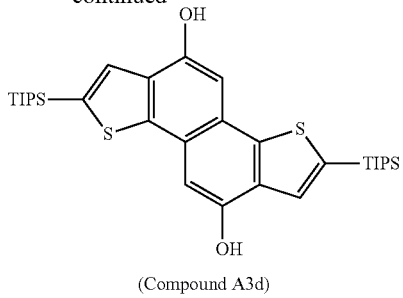

(Compound A3d)

Measurement data for the compound A3d obtained is given below.

$^1$H NMR (500 MHz, CDCl$_3$) δ, 1.19 (d, 36H, CH$_3$), 1.46 (sept, 6H, CH), 5.27 (s, 2H, OH), 7.26 (s, 2H, ArH), 7.74 (s, 2H, ArH) $^{13}$C NMR δ 12.0, 18.8, 102.9, 122.4, 129.8, 131.2, 135.0, 143.3, 147.9; EIMS (70 eV) m/z 584 (M$^+$).

In addition, a further functionalization was carried out using the compounds A3a and A3d obtained in Examples of Synthesis 11 and 14.

Example of Synthesis 15

Synthesis of 5,10-dihexadecyl-2,7-bis(triisopropylsilyl)naphtho[1,2-b:5,6-b']dithiophene (Hereinafter, the Compound A4aa)

A solution was prepared by stirring a 9-BBN solution (0.5 M solution in THF, 3 ml, 1.5 mmol) and 1-hexadecyne (0.4 ml, 1.5 mmol) at room temperature for six hours, and PdCl$_2$ (dppf) (41 mg, 0.05 mmol) and the compound A3a (355 mg, 0.5 mmol) were further added into the solution then, with a base, that is, a degassed THF (10 ml) used as a solvent, a NaOH solution (1 ml of 1.5 M solution) was added and refluxed for 15 hours. After being cooled, the mixture was diluted with chloroform, and an organic phase was concentrated after washed with water, and by purifying a residue by column chromatography (silica gel, chloroform), the compound A4aa was obtained as a white solid (245 mg, 51%).

[Chemical formula 32]

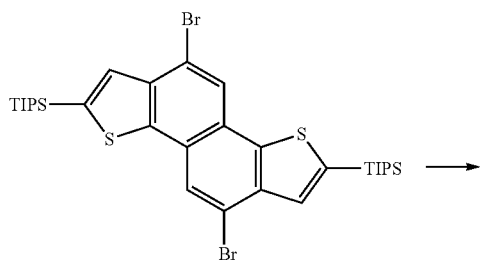

(Compound A3a)

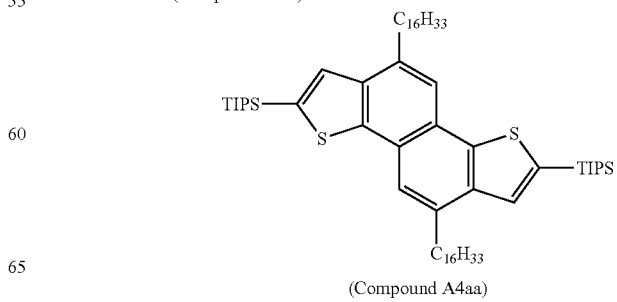

(Compound A4aa)

Measurement data for the compound A4aa obtained is given below.

$^1$H NMR (500 MHz, CDCl$_3$) δ 0.88 (t, 6H, CH$_3$) 1.20 (d, 36H, CH$_3$), 1.25-1.37 (m, 52H, CH$_2$), 1.48 (sept, 6H, CH), 1.82 (quint, 4H, CH$_2$), 3.09 (t, 4H, CH$_2$), 7.68 (s, 2H, ArH), 7.78 (s, 2H, ArH) $^{13}$C NMR δ 12.0, 14.3, 18.8, 22.8, 22.9, 29.5, 29.7, 29.8, 29.8, 29.8, 29.8, 29.9, 31.0, 31.7, 32.1, 34.5, 120.0, 124.8, 132.0, 134.2, 135.9, 138.6, 142.4; MS (MALDI-TOF, 1,8,9-trihydroxyanthracene matrix) m/z 100.76 (M$^+$).

Example of Synthesis 16

Synthesis of 5,10-bis(methoxycarbonyl)-2,7-bis(triisopropylsilyl)naphtho[1,2-b:5,6-b']dithiophene (Hereinafter, the Compound A4ab)

After n-BuLi (0.4 ml, 0.7 mmol, 1.65 M) was added into a THF (10 ml) solution of the compound A3a (200 mg, 0.3 mmol) at zero degree Celsius, the mixture was stirred at room temperature for 30 minutes, then methyl chlorocarbonate (0.06 ml, 0.78 mmol) was added. Subsequent to stirring at room temperature for 16 hours, water (5 ml) and 1N hydrochloric acid (5 ml) were added, then the mixture was extracted with chloroform. A concentrated extract is purified by column chromatography (silica gel, chloroform), and the compound A4ab (76 mg, 41%) is obtained as a yellow solid.

[Chemical formula 33]

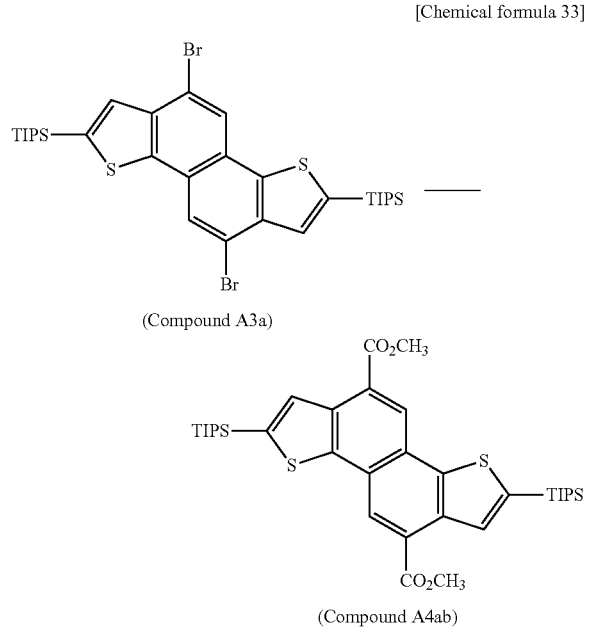

(Compound A3a)

(Compound A4ab)

Measurement data for the compound A4ab obtained is given below.

$^1$H-NMR (500 MHz, CDCl$_3$) δ 1.21 (d, 36H, CH3), 1.51 (sept, 6H, CH), 4.09 (s, 2H, CH$_3$), 8.55 (s, 2H, ArH), 8.89 (s, 2H, ArH), $^{13}$C NMR δ 12.1, 18.8, 125.3, 125.6, 126.8, 134.3, 136.9, 137.4, 145.4, 167.0; EIMS (70 eV) m/z 668 (M$^+$).

Example of Synthesis 17

Synthesis of 5,10-bis(methoxycarbonyl)-2,7-bis(triisopropylsilyl)naphtho[1,2-b:5,6-b']dithiophene (Hereinafter, the Compound A4d)

Subsequent to stirring the compound A3d (200 mg, 0.3 mmol) and potassium carbonate (100 mg, 0.7 mmol) in DMF (10 ml) at room temperature for two hours, 1-bromododecane (0.3 ml, 1.1 mmol) was added and stirred at 80° C. for 15 hours. After being cooled, the mixture was further added with water (5 ml) and 1N hydrochloric acid (5 ml), then was extracted using chloroform. After being concentrated, purification was carried out by column chromatography (silica gel, chloroform), and the compound A4d was obtained as a white solid (262 mg, 84%).

[Chemical formula 34]

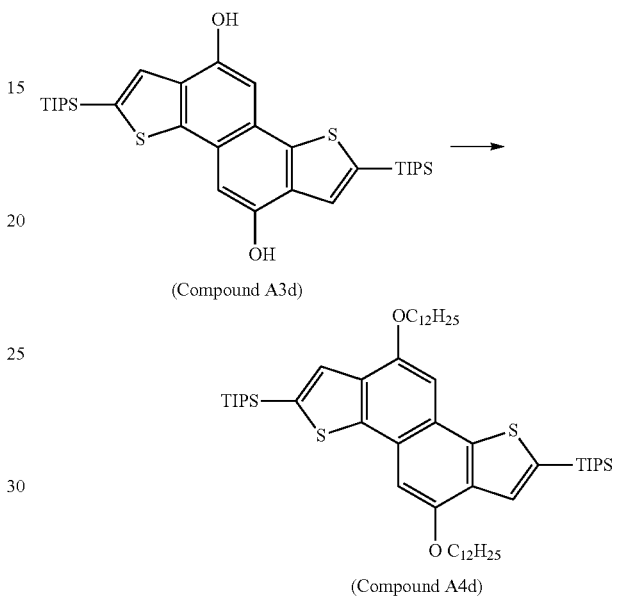

(Compound A3d)

(Compound A4d)

Measurement data for the compound A4d obtained is given below.

$^1$H NMR (500 MHz, CDCl$_3$) δ 0.88 (t, 6H, CH$_3$) 1.19 (d, 36H, CH$_3$), 1.25-1.37 (m, 52H, CH$_2$), 1.46 (sept, 6H, CH), 1.97 (quint, 4H, CH$_2$), 4.26 (t, 4H, CH$_2$), 7.15 (s, 2H, ArH), 7.70 (s, 2H, ArH) $^{13}$C NMR δ 12.1, 14.3, 18.8, 22.8, 26.4, 29.4, 29.5, 29.6, 29.8, 29.8, 29.9, 32.1, 68.5, 99.2, 122.3, 130.8, 132.4, 134.0, 143.2, 151.8; MS (MALDI-TOF, 1,8,9-trihydroxyanthracene matrix) m/z 920.64 (M$^+$).

Further, triisopropylsilyl-substituted benzodichalcogenophene was synthesized using various unsubstituted benzodichalcogenophene.

Example of Synthesis 18

Synthesis of 2,6-bis(triisopropylsilyl)benzo[1,2-b:4,5-b']difuran (Hereinafter, the Compound F1)

Other than using benzo[1,2-b:4,5-b']difuran instead of naphtho[1,2-b:5,6-b']dithiophene, the compound F1 was obtained in the same way described in Example of Synthesis 1.

[Chemical formula 35]

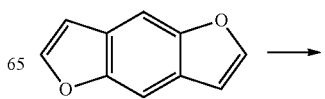

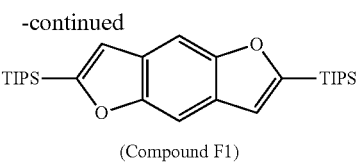

(Compound F1)

Measurement data for the compound F1 obtained is given below.

88% yield. $^1$H NMR (400 MHz, CDCl$_3$) δ 1.14 (d, 36H, CH3), 1.41 (sept, 6H, CH), 7.06 (s, 2H, ArH), 7.60 (s, 2H, ArH); $^{13}$C NMR δ 161.9 155.1 126.3 118.4 101.1 18.7 11.2; EIMS (70 eV) m/z=470 (M$^+$).

Example of Synthesis 19

Synthesis of 2,6-bis(triisopropylsilyl)benzo[1,2-b:4,5-b']dithiophene (Hereinafter, the Compound G1)

Other than using benzo[1,2-b:4,5-b']dithiophene instead of naphtho[1,2-b:5,6-b']dithiophene, the compound G1 was obtained in the same way described in Example of Synthesis 1.

[Chemical formula 36]

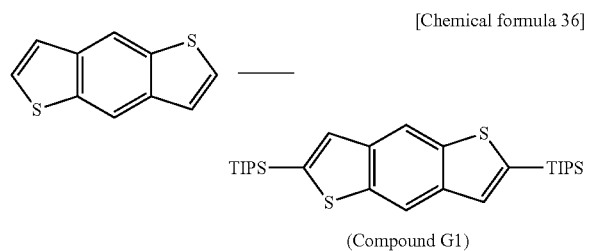

(Compound G1)

Measurement data for the compound G1 obtained is given below.

88% yield. $^1$H-NMR (500 MHz, CDCl$_3$) δ 1.16 (d, 36H, CH$_3$), 1.43 (sept, 6H, CH), 7.51 (s, 2H, ArH), 7.30 (s, 2H, ArH), $^{13}$C NMR δ 12.0, 18.8, 115.7, 131.7, 138.4, 139.0, 140.7; EIMS (70 eV) m/z 502 (M$^+$).

Example of Synthesis 20

Synthesis of 2,6-bis(triisopropylsilyl)benzo[1,2-b:4,5-b']diselenophene (Hereinafter, the Compound H1)

Other than using benzo[1,2-b:4,5-b']diselenophene instead of naphtho[1,2-b:5,6-b']dithiophene, the compound H1 was obtained in the same way described in Example of Synthesis 1.

[Chemical formula 37]

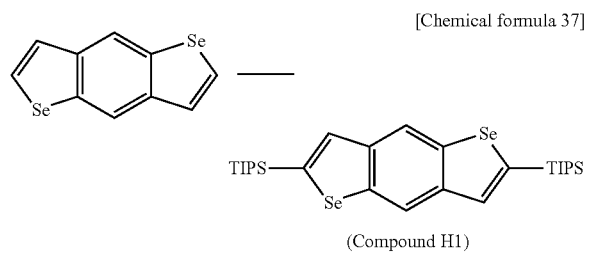

(Compound H1)

Measurement data for the compound H1 obtained is given below.

Quantitative yield. $^1$H-NMR (500 MHz, CDCl$_3$) δ 1.16 (d, 36H, CH$_3$), 1.39 (sept, 6H, CH), 7.77 (s, 2H, ArH), 8.36 (s, 2H, ArH), $^{13}$C NMR δ 12.2, 18.8, 121.2, 135.5, 140.9, 141.6, 142.3; EIMS (70 eV) m/z 598 (M$^+$).

Each triisopropylsilyl-substituted benzo[1,2-b:4,5-b'] dichalcogenophene (the compounds F1, G1, and H1) obtained in Examples of Synthesis 18 to 20 was directly boronized and a corresponding intermediate for the benzodichalcogenophene derivative was synthesized.

Example of Synthesis 21

Synthesis of 4,8-bis(4,4,5,5-tetramethyl-1,3,2-dioxaborolan-2-yl)-2,6-bis(triisopropylsilyl)benzo[1,2-b:4,5-b']difuran (Hereinafter, the Compound F2)

The compound F1 (1 mmol), pinacol diborane (2 mmol), [Ir(OMe)(COD)]$_2$ (5 mol %), and a dried cyclohexane solution of 4,4'-di-t-butyl-2,2'-bipyridine were stirred for 10 hours under argon atmosphere and shielded light at 80° C. After that, pinacol diborane (2 mmol), [Ir(OMe)(COD)]$_2$ (5 mol %), 4,4'-di-t-butyl-2,2'-bipyridine (10 mol %) were added five times at every five hours to accelerate the reaction. After the reaction mixture was cooled, a solvent was removed by distillation, a residue was dissolved in chloroform, a purification was carried out by column chromatography (silica gel, chloroform), and the compound F2 was obtained as a white solid.

[Chemical formula 38]

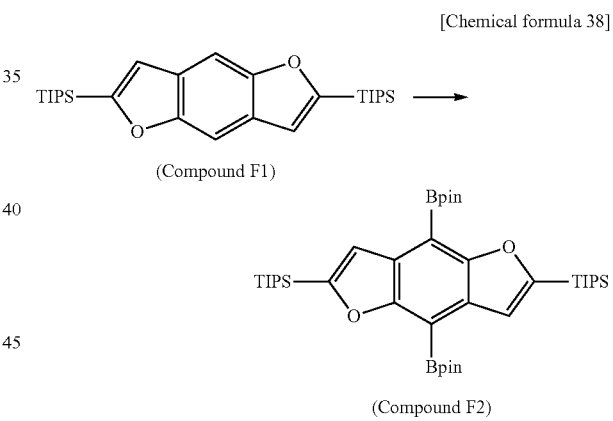

Measurement data for the compound F2 obtained is given below.

97% yield. $^1$H NMR (500 MHz, CDCl$_3$) δ 0.57 (m, 36H, CH$_3$), 1.37 (s, 24H, CH$_3$), 7.40 (s, 2H, ArH); $^{13}$C NMR δ 161.9 159.3 130.8 119.3 101.6 83.5 24.9 18.9 11.6; EIMS (70 eV) m/z=723 (M$^+$).

Example of Synthesis 22

Synthesis of 4,8-bis(4,4,5,5-tetramethyl-1,3,2-dioxaborolan-2-yl)-2,6-bis(triisopropylsilyl)benzo[1,2-b:4,5-b']dithiophene (Hereinafter, the Compound G2)

Other than using the compound G1 instead of the compound F1, the compound G2 was synthesized in the same way described in Example of Synthesis 21.

[Chemical formula 39]

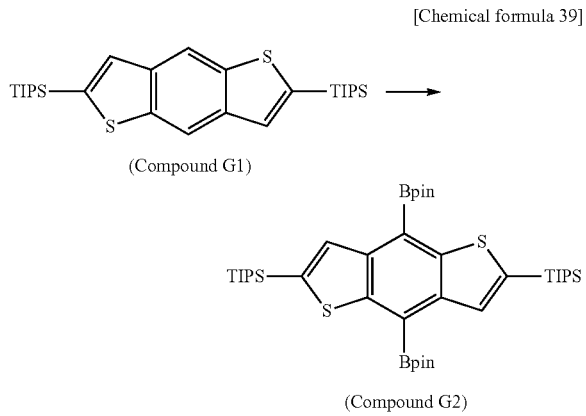

Measurement data for the compound G2 obtained is given below.

74% yield. $^1$H-NMR (500 MHz, CDCl$_3$) δ 1.18 (d, 36H, CH$_3$), 1.43 (sept, 6H, CH), 1.46 (s, 24H, CH$_3$), 8.30 (s, 2H, ArH) $^{13}$C NMR δ 12.2, 18.9, 25.2, 84.2, 134.0, 138.7, 143.5, 148.2; EIMS (70 eV) m/z 754 (M$^+$).

Example of Synthesis 23

Synthesis of 4,8-bis(4,4,5,5-tetramethyl-1,3,2-dioxaborolan-2-yl)-2,6-bis(triisopropylsilyl)benzo[1,2-b:4,5-b']diselenophene (Hereinafter, the Compound H2)

Other than using the compound H1 instead of the compound F1, the compound H2 was obtained in the same way described in Example of Synthesis 21.

[Chemical formula 40]

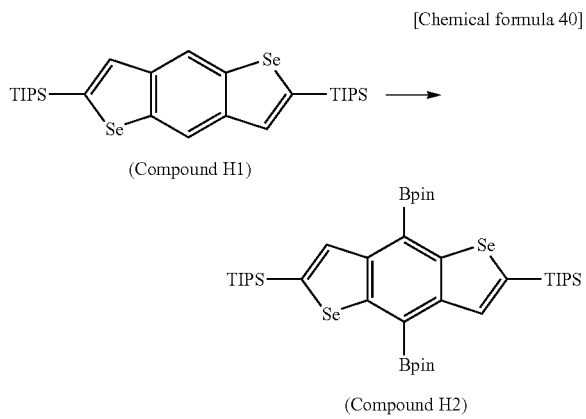

Measurement data for the compound H2 obtained is given below.

28% yield. $^1$H-NMR (500 MHz, CDCl$_3$) δ 1.19 (d, 36H, CH$_3$), 1.40 (sept, 6H, CH), 1.45 (s, 24H, CH$_3$), 8.72 (s, 2H, ArH) $^{13}$C NMR δ 12.4, 19.0, 25.2, 84.4, 138.0, 142.2, 145.8, 150.1; EIMS (70 eV) m/z 850 (M$^+$).

Having described, it will be evident that various modifications and changes may be made without departing from the spirit and scope of the present disclosure. In the foregoing specification, the embodiments are to be regarded in an illustrative rather than a restrictive sense.

The present application claims priority to Japanese Patent Application No. 2012-031605, filed Feb. 16, 2012. Further, the present application incorporates by reference the entire specification and the claims of Japanese Patent Application No. 2012-031605.

INDUSTRIAL APPLICABILITY

The intermediate for the acenedichalcogenophene derivative and the method for synthesizing thereof disclosed herein are expected to be utilized for research, developments, and practical applications of the organic semiconductor materials having novel acenedichalcogenophene skeleton.

The invention claimed is:

1. An intermediate for an acenedichalcogenophene derivative of formula (1) or formula (2),

[Chemical formula 1]

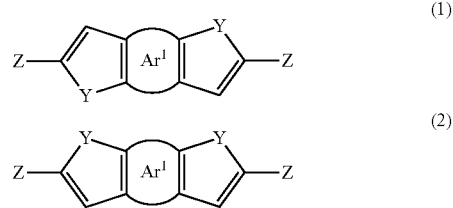

(in formulae (1) and (2), Ar$^1$ represents any one ring of a benzene ring, a naphthalene ring, or an anthracene ring having at least one of hydrogens thereof that is substituted with a boronic acid group or a boronate ester group; Y represents an oxygen atom, a sulfur atom, or a selenium atom; and Z represents a substituent group).

2. The intermediate for the acenedichalcogenophene derivative according to claim 1, wherein the acenedichalcogenophene derivative of the formula (1) is expressed by formula (11), formula (21) formula (22) or formula (23),

[Chemical formula 2]

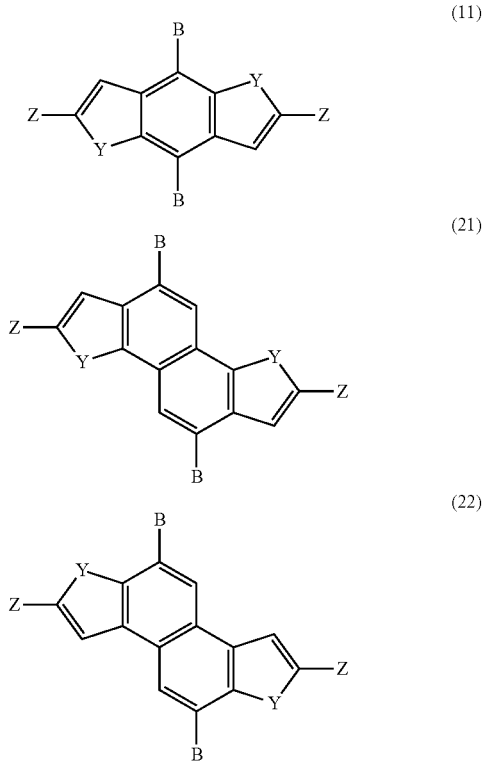

-continued (23)

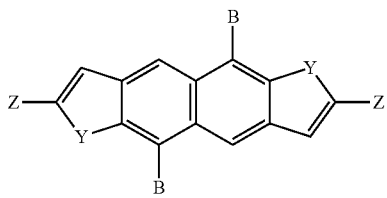

(in formulae (11), (21), (22) and (23), B represents a boronic acid group or a boronate ester group, and Y and Z are as defined for the formula (1)).

3. The intermediate for the acenedichalcogenophene derivative according to claim 1, wherein the substituent group is expressed by any one of formulae (41) to (45),

[Chemical formula 3]

—R      (41)

—SiR$_3$      (42)

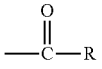      (43)

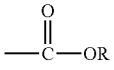      (44)

—X      (45)

(wherein, in the formulae (41) to (45), R represents an alkyl group, an aryl group, or a phenylmethyl group, and X represents halogen).

4. The intermediate for the acenedichalcogenophene derivative according to claim 1, wherein the boronate ester group is a pinacol boronate ester group.

* * * * *